United States Patent [19]
Li

[11] Patent Number: 5,439,470
[45] Date of Patent: Aug. 8, 1995

[54] SUTURE THROW RUNDOWN TOOL

[75] Inventor: Lehmann K. Li, Wellesley, Mass.

[73] Assignee: Li Medical Technologies, Inc., Shelton, Conn.

[21] Appl. No.: 242,030

[22] Filed: May 12, 1994

Related U.S. Application Data

[63] Continuation of Ser. No. 958,913, Oct. 9, 1992, abandoned.

[51] Int. Cl.⁶ ............................................. A61B 17/00
[52] U.S. Cl. ................................. 606/148; 606/139; 289/17
[58] Field of Search ............................ 606/1, 106–108, 606/110–112, 139, 144, 148, 205–209; 289/17; 604/158, 160, 166, 164

[56] References Cited

U.S. PATENT DOCUMENTS

| | | | |
|---|---|---|---|
| 1,625,602 | 4/1927 | Gould et al. | 606/139 |
| 3,828,791 | 8/1974 | Santos | 606/207 |
| 4,935,027 | 6/1990 | Yoon | 606/148 |
| 4,961,741 | 10/1990 | Hayhurst | 606/139 |
| 5,015,250 | 5/1991 | Foster | 606/148 |
| 5,176,691 | 1/1993 | Pierce | 606/148 |

FOREIGN PATENT DOCUMENTS

| | | | |
|---|---|---|---|
| 0912619 | 5/1954 | Germany | 606/139 |
| 2454371 | 6/1975 | Germany | 606/205 |

Primary Examiner—Stephen C. Pellegrino
Assistant Examiner—Jeffrey A. Schmidt
Attorney, Agent, or Firm—Pandiscio & Pandiscio

[57] ABSTRACT

An improved suture throw rundown tool particularly useful in laparascopic and similar surgical procedures is provided which includes an elongated shaft having a proximal end and a first distal tip, an elongated rod extending through the shaft in reciprocating relation therewith and having a proximal end and a second distal tip, and a control device connected between the shaft and the rod for controlling the relative disposition of the first and second distal tips. The first and second distal tips are specially designed to mate with each other in a first position and to be longitudinally offset relative to each other in a second position. In the offset position, a suture throw may be engaged by the distal end of one of the distal tips while the free ends of the suture emanating therefrom are extended through grooves connecting the distal end of the offset distal tip to its outer edge. Movement of the distal tips from their offset configuration to their aligned configuration provides a distally facing suture throw engagement portion flanked by closed passageways for the free suture ends emanating from the suture throw which prevent dislodgement of the throw from the tool during the rundown operation. A capability for trimming free suture ends emanating from a completed surgical knot at an internal surgical site are also provided.

14 Claims, 11 Drawing Sheets

SUTURE THROW RUNDOWN TOOL

This is a continuation of application(s) Ser. No. 07/958,913 filed on Oct. 9, 1992, now abandoned.

FIELD OF THE INVENTION

The present invention relates generally to surgical instruments. More particularly, the invention relates to suture throw rundown tools, and still more specifically, to suture throw rundown tools suitable for use in laparascopic surgical procedures and the like.

BACKGROUND OF THE INVENTION

Conventional suturing practices remain the procedures of choice for many specific surgical applications, and indeed for many surgeons generally. In conventional suturing, a length of suture is extended through (or around) the objects to be attached together, and the suture is thereafter secured by tying a knot in the two free ends of the suture.

For example, the length of suture might be threaded downwardly through tissue on one side of an incision, then below the incision itself, and finally upwardly through the tissue on the other side of the incision, so that the free ends of the suture will extend out of the tissue on either side of the incision, and the intermediate portion of the suture will extend across the incision. Thus, the two free ends of suture extend outwardly from the surgical site. Conventional surgical knots then are formed in the two free suture ends so as to secure the objects together. Typically, such surgical knots include at least two throws which are separately formed and then drawn tight, one on top of the other, against the objects being joined, in a manner similar to the tying of the well-known square knot.

In many situation the surgical site is relatively accessible to the surgeon, e.g. during a conventional "open" surgical procedure. In other situations, however, the surgical site may be at an interior location and access to the site might be through tiny portals, e.g. a laparoscopic surgical procedure. In this case, the surgeon can form the suture throws internally, using instruments manipulated from outside of the body, or the surgeon can form the suture throws externally and then run them down the suture ends to the surgical site.

In the situation where the suture throws are to be formed externally and then run down the suture ends to the surgical site, the small access portals used and the significant rundown distances involved can make it difficult or even impossible for the surgeon to draw each throw tightly against the surgical site simply by pulling the respective free ends of the suture apart, as is conventionally done in forming a well-known square knot. As a result, suture throw rundown tools have been developed for pushing the individual throws (which are formed outside of the body) down the suture ends so that they bear tightly against the objects which are to be joined. Typically, these tools have included a shaft having a depression in its distal end which is adapted to seat a suture throw therein. In use, a throw is formed in the two free ends of the suture outside of the body. Then, while tension is maintained on the two free suture ends, the throw is engaged by the distal end of the tool so that the throw is seated in the tool's front depression. Thereafter, the tool is forced down the suture lengths, passing through the access portal, so as to transfer the throw to the surgical site where it will assume a position bearing against the objects to be joined.

It has been found, however, that maintaining the desired amount of tension on the two free suture ends during throw rundown can be cumbersome and difficult in some situations. Furthermore, the suture throw can sometimes slip out of engagement with the depression at the distal end of the rundown tool. In these situations it can often be difficult, if not impossible, to re-engage the throw so as to successfully move it all the way down to the surgical site. Still further, it has been found that there is a need in the art for the capability to conveniently, safely and reliably trim the free suture ends remaining after the surgical knot has been formed at an internal surgical site.

OBJECTS AND SUMMARY OF THE INVENTION

Accordingly, one object of the present invention is to provide an improved suture throw rundown tool for engaging and pushing a suture throw down the two free suture ends extending away from a surgical site, wherein the tool is adapted to minimize the possibility of the suture throw becoming accidentally disengaged from the rundown tool.

Another object of the present invention is to provide an improved suture throw rundown tool which simplifies maintaining the desired amount of tension on the two free suture ends during throw rundown.

Still another object of the present invention is to provide an improved suture throw rundown tool which includes means for conveniently, safely and reliably trimming the free ends of the suture remaining after a surgical knot has been formed at an internal surgical site.

These and other objects of the present invention are accomplished by the provision of an improved suture throw rundown tool. In its preferred embodiment, the rundown tool includes a handle assembly, a shaft and a translation assembly.

The shaft is fixedly attached to the handle assembly at its proximal end, and includes a specially designed first distal tip.

The translation assembly includes a rod which extends through the shaft and which is reciprocally movable therein. The rod has a specially designed second distal tip, and is attached to the handle at its proximal end by biasing means which are adapted to yieldably urge the rod toward its proximalmost position relative to the shaft. The translation assembly also includes trigger means pivotally connected attached to the handle and engaging the proximal portion of the rod wherein the trigger means are adapted to axially move the rod through the shaft from its proximalmost position to a distalmost position.

The first and second distal tips matingly engage one another in longitudinally reciprocal, sliding relation along a plane which contains the longitudinal axis of the shaft. Further, the mating surfaces of the first and second distal tips define corresponding projections and projection-receiving portions, respectively, as well as various grooves. These structures are configured relative to one another along the mating plane so that when the rod is in its proximalmost position, the first and second distal tips together define distally facing, suture throw engagement means for engaging a suture throw, with the suture throw engagement means being flanked by two passageways. These two passageways are adapted to receive the two free suture ends which extend from the opposite sides of the suture throw, such that those suture ends may slide through their respective passageways as the throw is run down to the surgical site.

The first and second distal tips are also constructed so that when the rod is in its distalmost position, grooves in the second distal tip (which form one side of the aforementioned flanking passageways) are located distally of the distal end of the first distal tip, so as to provide access to those grooves.

In this way, the trigger means can be actuated so as to place the rod in its distalmost position, whereby the two free suture ends can be placed in their respective grooves and then released so that the biasing means will return the rod to its proximalmost position, thereby slidably capturing the two free suture ends to the tool within their respective passageways. The suture throw can then be run down to the surgical site without fear of the suture throw departing from the rundown tool. The suture can thereafter be released from the tool simply by actuating the trigger means so as to once again place the rod in its distalmost position, thus exposing the groove and permitting the suture to be separated from the tool.

Still further, a cutting blade may be disposed between the first and second distal tips, substantially along the plane of their mating engagement, so as to be conveniently accessible through corresponding slots provided in each of the first and second tips. These slots are located in a plane oriented generally normally to both the throw-engaging end of the tip assembly and the plane along which the first and second tips are mated.

In a presently preferred form of the invention, it has been found convenient to form the second distal tip as a separate element from the rod, and to hingedly connect the proximal end of the second distal tip to the distal end of the rod. In this way the second distal tip may be swung away from the first distal tip thereby allowing convenient access to the cutting blade disposed between the first and second distal tips, e.g. for replacement purposes. In such a construction, a locking sleeve is used to maintain the normal longitudinal orientation of the first and second distal tips relative to each other. This sleeve can be moved proximally relative to the distal end of the tool when it is desired to swing the second distal tip away from the first distal tip.

The new suture throw rundown tool is generally used as follows:

(1) a throw is formed in the two free ends of the suture extending away from the internal surgical site;

(2) the trigger means are manipulated so as to move the rod from its proximalmost position to its distalmost position, thereby shifting the second distal tip distally relative to the first distal tip;

(3) the suture throw is positioned adjacent the distal end of the second distal tip, with the suture throw's two free suture ends being placed in the second distal tip's exposed grooves;

(4) the trigger means are released so that the second distal tip is allowed to slide proximally to its proximalmost position, thereby placing it in alignment with the first distal tip so that the first and second distal tips together define a suture throw engagement end and so that the two suture ends extending away from the suture throw are slidably captured in the aforementioned two passageways;

(5) the throw rundown tool is pushed towards the surgical site, so as to run the suture throw down to the surgical site;

(6) then, either before or after the tool has been withdrawn from the internal surgical site, the trigger means is actuated again so as to slide the second tip distally relative to the first tip, thereby exposing the second tip's suture-receiving grooves and permitting the suture ends to slip free from the rundown tool; and (7) the foregoing procedure is repeated as many times as required to form the desired surgical knot.

After the knot has been formed and the two free suture ends freed from the tool, the suture ends can be trimmed from the knot by maintaining tension on the suture ends, rotating the rundown tool 90 degrees, drawing the two ends of the suture into the transverse slots and into engagement with the blade, and then pushing the tool forward so as to sever the suture ends with the blade.

BRIEF DESCRIPTION OF THE DRAWINGS

Numerous other details of the construction of the preferred embodiment of the invention will become apparent to those skilled in the art in view of the following detailed description of the preferred embodiment which is rendered hereinbelow in conjunction with the accompanying drawings in which.

DETAILED DESCRIPTION OF PREFERRED EMBODIMENT

Figure 1:
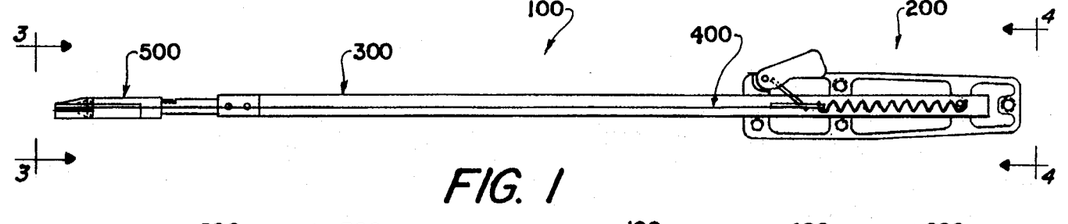
FIG. 1 is a side elevational view, in cross-section, of the left side of a suture rundown throw tool formed in accordance with the present invention.
Figure 2:
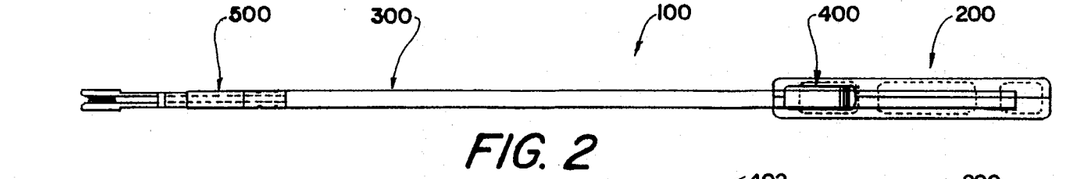
FIG. 2 is a top elevational view of the rundown tool shown in FIG. 1.
Figure 3:
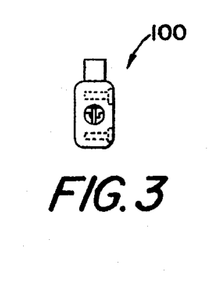
FIG. 3 is an end view of the rundown tool shown in FIG. 1, taken along line 3—3 of FIG. 1.
Figure 4:
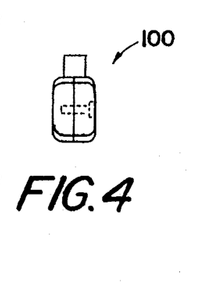
FIG. 4 is an end view of the rundown tool shown in FIG. 1, taken along line 4—4 of FIG. 1.
Figure 5:
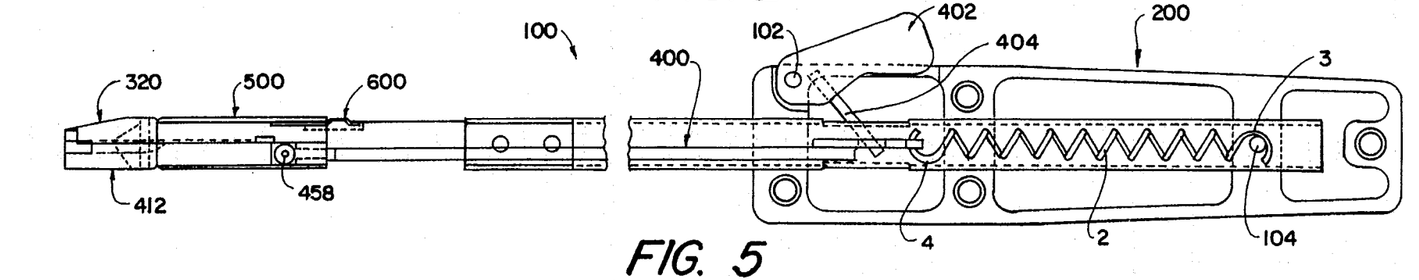
FIG. 5 is an enlarged, partially cut away, side elevational view showing the left side of the rundown tool shown in FIG. 1.
Figure 6:
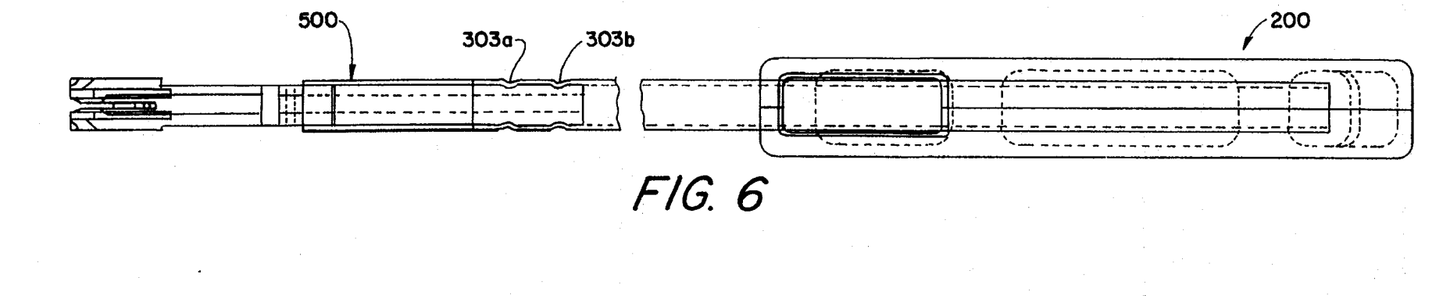
FIG. 6 is an enlarged, partially cut away, top elevational view of the rundown tool shown in FIG. 1.
Figure 7:
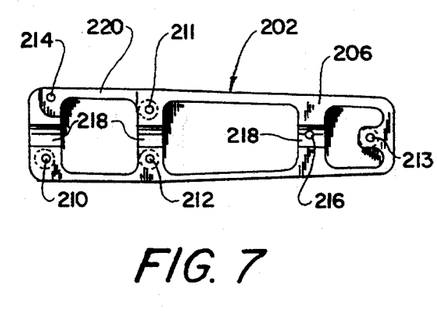
FIG. 7 is a side elevational view showing the interior side of the right half of the rundown tool's handle.
Figure 8:
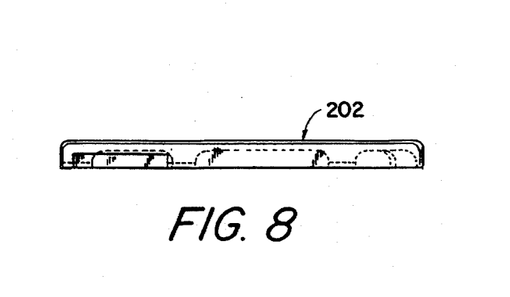
FIG. 8 is a top elevational view of the right handle half shown in FIG. 7.
Figure 9:
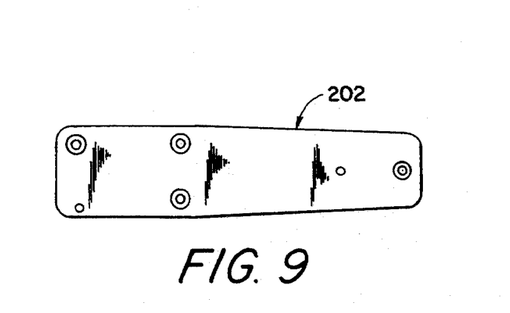
FIG. 9 is a side elevational view showing the exterior of the right handle half shown in FIG. 7.
Figure 10:
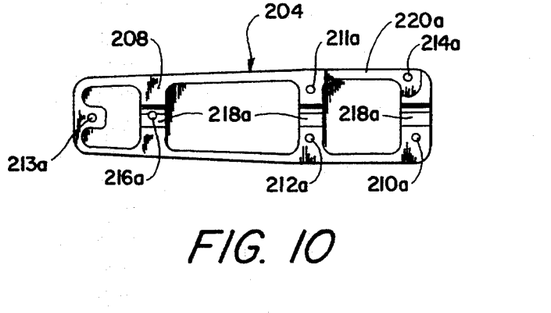
FIG. 10 is a side elevational view showing the interior side of the left half of the rundown tool's a handle.
Figure 11:
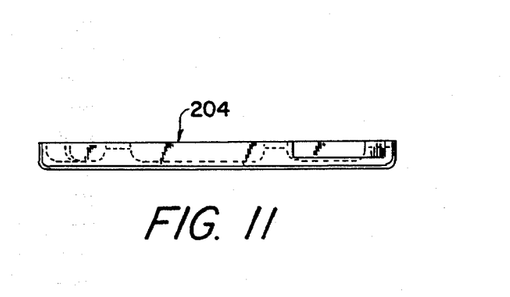
FIG. 11 is a bottom elevational view of the left handle half shown in FIG. 10.
Figure 12:
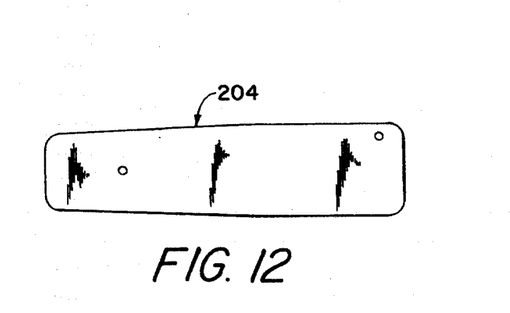
FIG. 12 is a side elevational view showing the exterior of the left handle half shown in FIG. 10.
Figure 13:
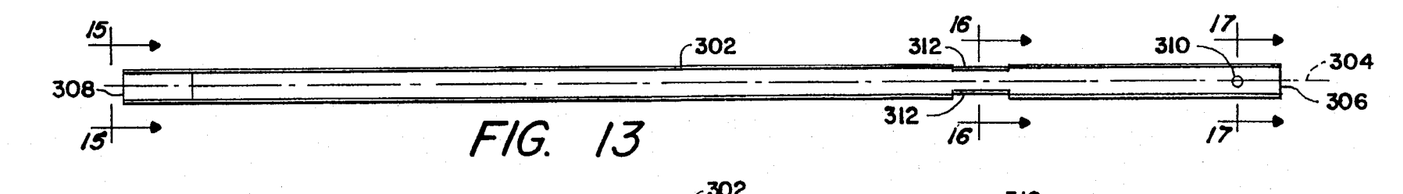
FIG. 13 is a side elevational view of the rundown tool's shaft.

Referring now to the drawings, and particularly to FIGS. 1–4, there are shown cross-sectional views of the left side, top, and left and right ends, respectively, of a preferred embodiment of an improved suture rundown tool formed in accordance with the present invention. The tool, generally indicated at 100, includes (a) a handle assembly, generally indicated at 200 (see FIGS. 7–12); (b) an elongated shaft, generally indicated at 300 (see FIGS. 13–29) affixed to the handle assembly; (c) a translation assembly, generally indicated at 400 (see FIGS. 25–38) which is reciprocally movable relative to the handle and shaft assemblies; and (d) a locking sleeve assembly, generally indicated at 500 (see FIGS. 40–47). Enlarged, partially cut away renditions of FIGS. 1 and 2 are provided in FIGS. 5 and 6, and enlarged views of the distal tip of the tool are provided in FIGS. 40–41 in order to facilitate an understanding of the following description of the various parts of the tool and the association of those parts with one another.

The handle assembly is shown in detail in FIGS. 5–12. Specifically, FIGS. 7–9 respectively show the inside, top and outside of a right-hand handle half 202 of a representative handle 200. Similarly, FIGS. 10–12 respectively show the inside, bottom and outside of a left-hand handle half 204 of the same handle.

Left-hand handle half 204 and right-hand handle half 202 mate together along their respective inside surfaces, generally indicated at 206 and 208, such that screw receiving holes 210, 211, 212 and 213 in right-hand handle half 202 are aligned with screw end receiving cavities 210a, 211a, 212a and 213a in left-hand handle half 204. Similarly, holes 214 and 216 in right-hand handle half 202 are aligned with holes 214a and 216a in left-hand handle half 204. Further, channel defining portions 218 in right-hand handle half 202 are aligned with channel defining portions 218a of left-hand handle half 204 in the mated configuration. Still further, elongated depressions 220 and 220a in the outer edges of the right-hand and left-hand handle portions, respectively, also are aligned in the assembled handle configuration so as to form a trigger receiving cavity, as will be discussed in more detail below.

The handle halves 202 and 204 are simply screwed together with screws (not shown), with pins 102 and 104 (FIG. 5) being inserted so as to extend between holes 214 and 214a, and 216 and 216a, respectively, to form the handle assembly per se.

The elongated shaft 300 is best seen in FIGS. 1, 2, 5, 6 and 13–24. Specifically, the shaft 300 includes an elongated tubular structure 302 having a longitudinal axis 304, a proximal end 306 and a distal end 308. A horizontal hole 310 extends through the tubular structure 302 substantially adjacent to its proximal end 306 and transverse to the longitudinal axis 304. Similarly, a vertical slot 312 extends through the tubular structure 302 from its top side to its bottom side at a location slightly distally of the location of hole 312.

A first distal tip structure 320 (best seen in FIGS. 18–24) extends distally from the distal end 308 of the tubular structure 302. First distal tip structure 320 may be formed integrally with the tubular structure 302. It has been found, however, that the telescopic insertion of the proximalmost portion 322 of the first distal tip 320 into the distal end 308 of the tubular structure 302, followed by the crimping of the walls of the tubular structure 302 adjacent its distal end 308 at selected locations 303a and 303b so as to set the tube against corresponding indentations 305a and 305b in the first distal tip 320 (see FIG. 6) is a both convenient and satisfactory alternative which can facilitate manufacture of the tool.

In essence, the first distal tip 320 includes a proximal portion 324 (incorporating proximalmost portion 322) and a distal portion 326. The cross-section of the proximal portion 324 transverse to the axis 304 is slightly smaller than the inner transverse cross-section of the tubular structure 302. The distal portion 326, on the other hand, includes a portion 328 extending distally from the proximal portion 324 above a horizontal plane, generally indicated by dotted line 325, which contains the axis 304.

The distalmost portion 330 of the distal portion 326 defines a pair of spaced, distally-extending arms 331 and 333 separated by a slot 332. Slot 332 extends from a transverse bore 334 to the distal end 336 of first distal tip 320. The distalmost portion 330 also defines a proximally facing shoulder 336 and a slanted, distally facing surface 338 extending at an acute angle to the horizontal plane 325. (FIG. 18) Downwardly extending projections 340 and 342 are located on the bottom surfaces 344 and 345 of the arms 331 and 333, respectively, immediately adjacent the distal end 334a of the first distal tip 320. The outer edges of each of the arms 331 and 333 are cut away at 329 and 329a, respectively, for reasons which will hereafter become apparent.

Figures 18, 19:
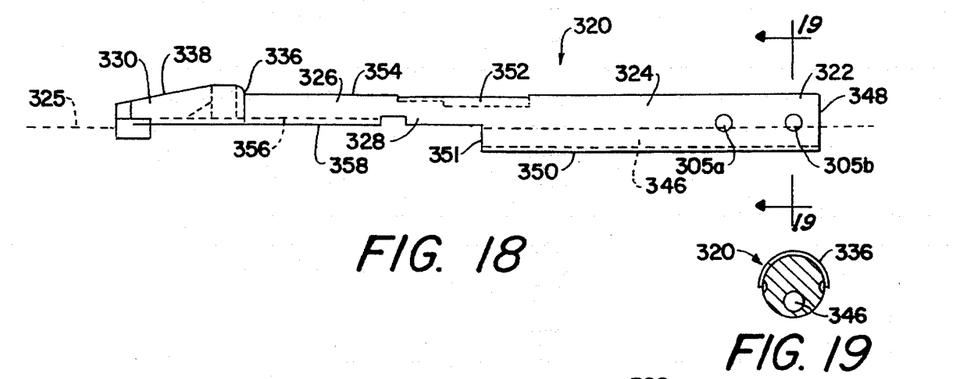
FIG. 18 is a side elevational view of the left side of the rundown tool's first distal tip.
FIG. 19 is a cross-sectional view of the first distal tip shown in FIG. 18, taken along line 19—19 of FIG. 18.
Figures 20, 21:
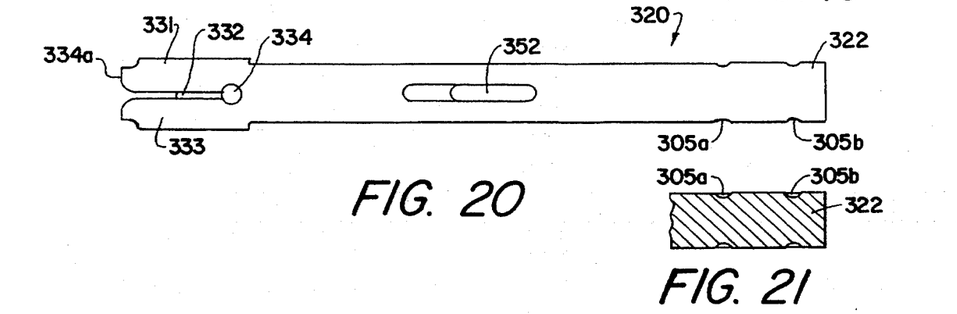
FIG. 20 is a top elevational view of the first distal tip shown in FIG. 18.
FIG. 21 is a partial cross-sectional view of the proximal end of the first distal tip shown in FIG. 20.
Figure 22:
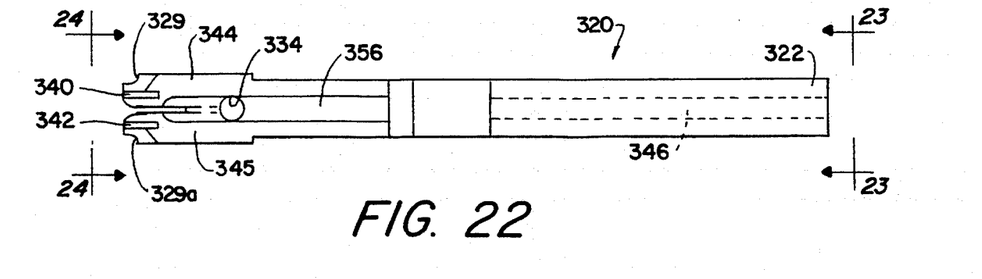
FIG. 22 is a bottom elevational view of the first distal tip shown in FIG. 18.
Figure 23:
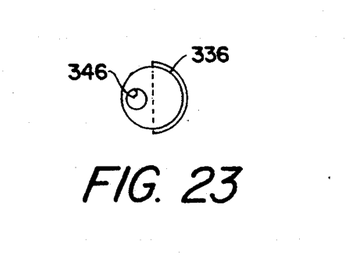
FIG. 23 is a right end view of the first distal tip shown in FIG. 22, taken along line 23—23 of FIG. 22.
Figure 24:
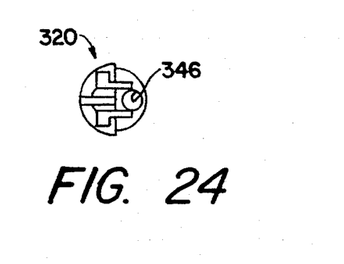
FIG. 24 is a left end view of the first distal tip shown in FIG. 22, taken along line 24—24 of FIG. 22.

The proximal portion 324 of first distal tip 320 defines a bore 346 extending from the proximal end 348 of the first distal tip 320 to the distal end 351 of the proximal portion 324. Bore 346 extends parallel to the plane 325, parallel to lower surface 350. The distal portion 326 of first distal tip 320 also defines a cavity 352 in its upper surface 354, and a slot 356 in its lower surface 358.

Returning now to FIG. 5, it will be seen that the portion of the tubular structure 302 adjacent to its proximal end 306 is located in the passageway formed by the channel portions 218 and 218a of the handle halves 202 and 204 when they are assembled together. The pin 104 engages the hole 310 in tubular structure 302 so that the tubular structure 302 is retained in a fixed position (both axially and rotationally) relative to the handle assembly 200.

Figures 14, 15, 16, 17, 25:
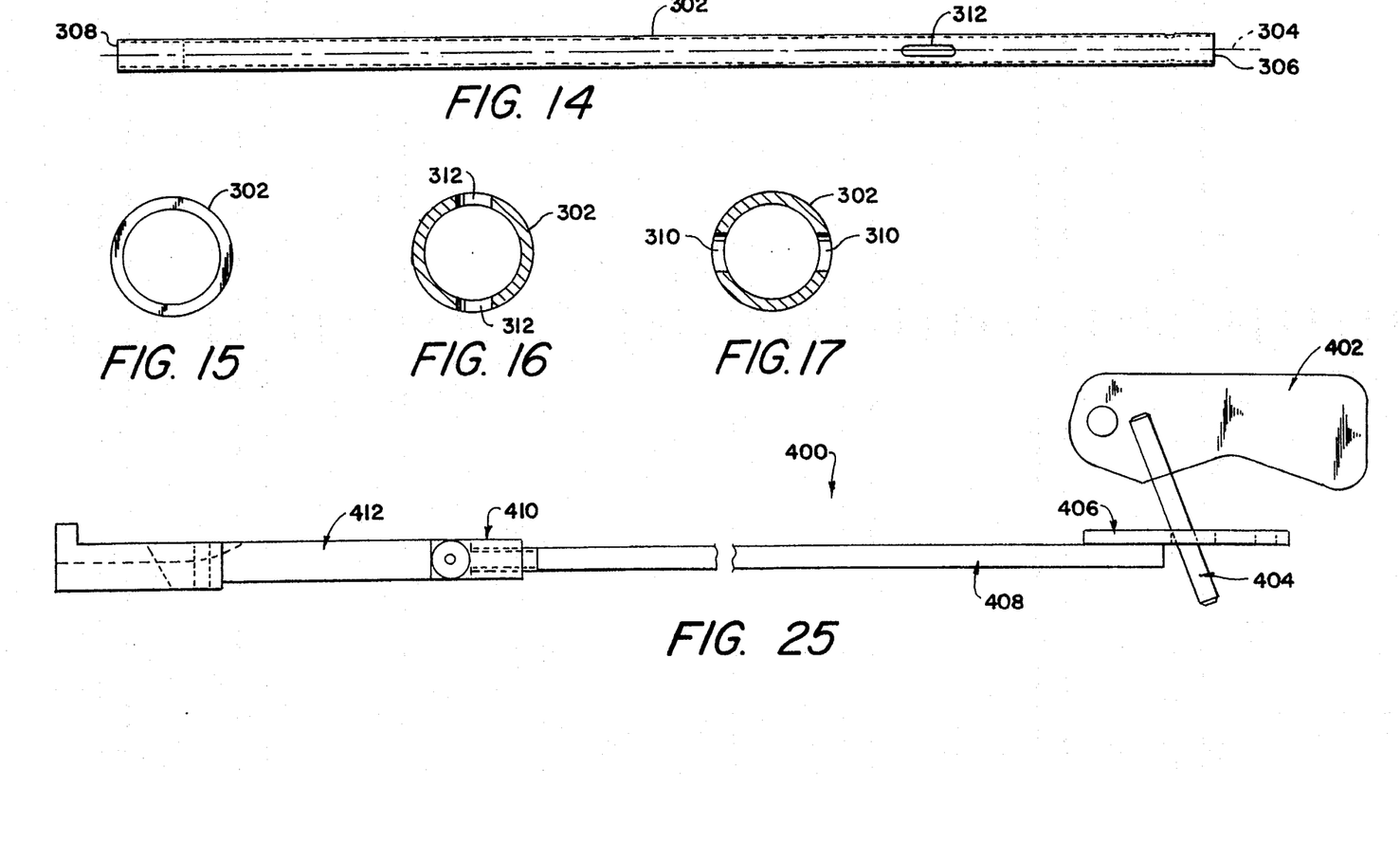
FIG. 14 is a top elevational view of the shaft shown in FIG. 13.
FIG. 15 is an end view of the shaft shown in FIG. 13, taken along line 15—15 of FIG. 13.
FIG. 16 is a cross-sectional view of the shaft shown in FIG. 13, taken along line 16—16 of FIG. 13.
FIG. 17 is a cross-sectional view of the shaft shown in FIG. 13, taken along line 17—17 of FIG. 13.
FIG. 25 is a left side elevational view showing the rundown tool's translation assembly, including the second distal tip, the rod and the trigger mechanism in operative association with the rod.
Figure 26:
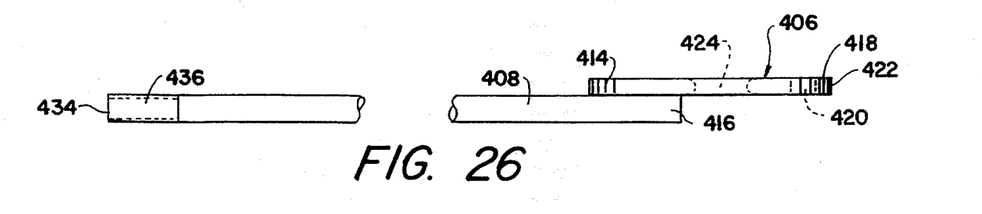
FIG. 26 is an enlarged left side elevational view, partially cut away, of the rod shown in FIG. 25.
Figure 27:
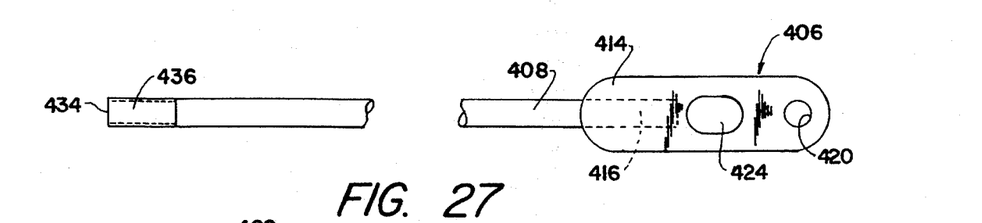
FIG. 27 is a top elevational view, partially cut away, of the rod shown in FIG. 26.
Figure 28:
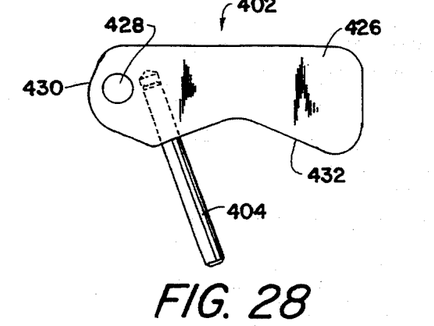
FIG. 28 is a left side elevational view of the tool's trigger mechanism.
Figure 29:
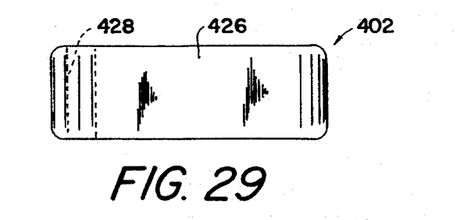
FIG. 29 is a top elevational view of the trigger element shown in FIG. 28.
Figure 30:
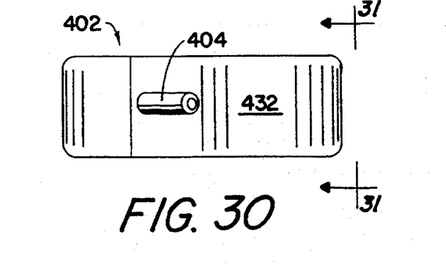
FIG. 30 is a bottom elevational view of the trigger element shown in FIG. 28.
Figure 31:
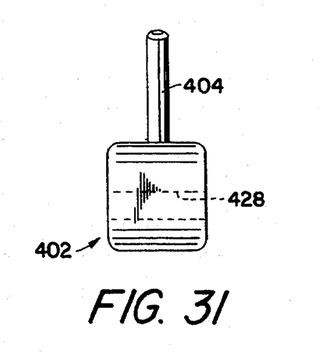
FIG. 31 is an end elevational view of the trigger element shown in FIG. 30, taken along line 31—31 of FIG. 30, with the view having been rotated 90 degrees clockwise from the position shown in FIG. 30.
Figure 32:
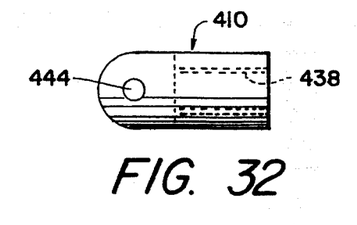
FIG. 32 is a left side elevational view of a hinge element used to connect the tool's rod to the second distal tip.
Figure 33:
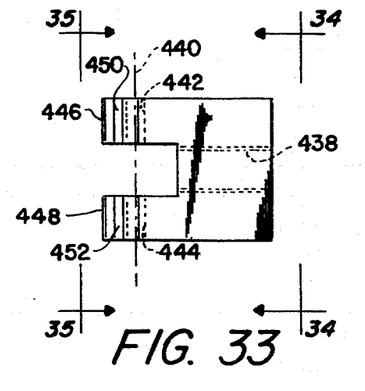
FIG. 33 is a top elevational view of the hinge shown in FIG. 32.
Figure 34:
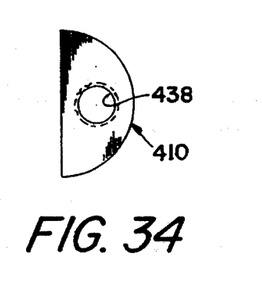
FIG. 34 is a right end elevational view of the hinge shown in FIG. 33, taken along line 34—34 of FIG. 33.
Figure 35:
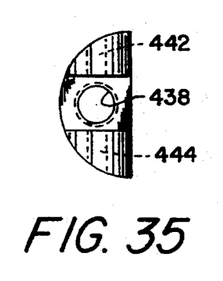
FIG. 35 is a left end elevational view of the hinge shown in FIG. 33, taken along the line 35—35 of FIG. 33.
Figure 36:
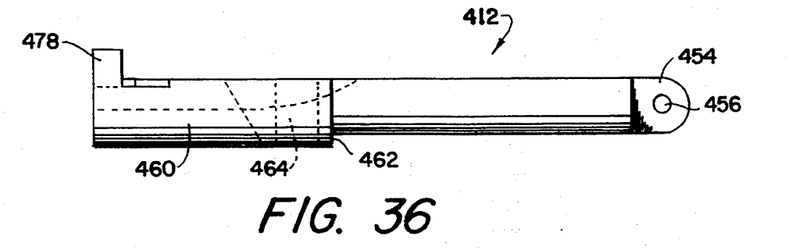
FIG. 36 is an enlarged left side elevational view of the tool's second distal tip.
Figures 37, 38, 39:
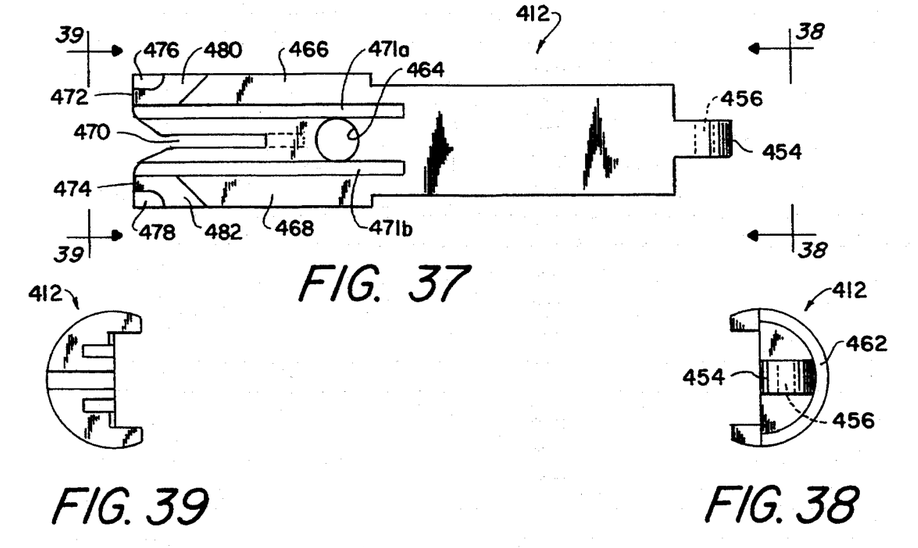
FIG. 37 is a top elevational view of the second distal tip shown in FIG. 36.
FIG. 38 is a right end elevational view of the second distal tip shown in FIG. 37, taken along line 38—38 of FIG. 37.
FIG. 39 is a left end elevational view of the second distal tip shown in FIG. 37, taken along line 39—39 of FIG. 37.

Turning now to the translation assembly 400 shown in FIGS. 25–38, and looking first at FIG. 25, it will be seen that assembly 400 includes a trigger 402, a projection 404 extending outwardly from trigger 402, a connecting plate 406, a connecting rod 408, a hinge member 410 and a second distal tip 412. As best seen in FIGS. 26 and 27, the distal portion 414 of connecting plate 406 is welded or otherwise fixedly attached to connecting rod 408 adjacent its proximal end 416. The proximal portion 418 of connecting plate 406, on the other hand, contains a transverse bore 420 located adjacent its proximal end 422 and a longitudinal transverse slot 424 located slightly distally of bore 420.

The trigger 402 (best seen in FIGS. 28–31) includes a finger engagement portion 426 defining a bore 428 adjacent its distal end 430. Projection 404 extends outwardly from the lower surface 432 of trigger 402, at an acute angle.

Connecting rod 408 is threaded adjacent its distal end 434 as representatively indicated at 436. Threaded bore 438 of hinge member 410 (FIGS. 32–34) is screwed onto the threaded portion 436 of connecting rod 408 such that the common axis 440 of bores 442 and 444 located adjacent the distal ends 446 and 448 of arms 450 and 452 is disposed substantially parallel to the horizontal plane 325 when the connecting rod 408 extends from the handle 200, through tubular structure 302 and through the bore 346 in first distal tip 320. (see FIGS. 5, 25 and 32–35).

Distally projecting tongue 454 of second distal tip 412 (FIGS. 36–38) is located between arms 450 and 452 of hinge 410 (FIG. 33) such that bore 456 extending through tongue 454 is aligned with bores 442 and 444. A pin 458 (FIG. 5) is then inserted through bores 442, 456 and 444 so as to hingedly attach second distal tip 412 to connecting rod 408. (see FIGS. 5 and 40–41)

Second distal tip 412 (FIGS. 36–39) is sized to mate with first distal tip 320 along the horizontal plane 325. Accordingly, the distalmost portion 460 of second distal tip 412 defines (i) a proximally facing shoulder 462 corresponding to shoulder 336, (ii) a transverse bore 464 corresponding to bore 334 (FIG. 20), and (iii) distally extending arms 466 and 468 (separated by a longitudinal slot 470) corresponding to arms 331 and 333 (and slot 332) of first distal tip 320 (FIG. 20). In addition, arms 466 and 468 include longitudinal slots 471a and 471b extending proximally from the distal ends 472 and 474 of the arms 466 and 468. Slots 471a and 471b are adapted to receive the downwardly extending projections 340 and 342 from first distal tip 320 in slidable relation therein. Upwardly extending projections 476 and 478 are located at the outer edges of the distal ends of arms 466 and 468 so as to matingly engage the corresponding cut away sections 329 and 329a of the arms 331 and 333. Grooves 480 and 482 extend from the distal ends 472 and 474 of arms 466 and 468 to the outer edges of those arms, respectfully proximally adjacent to the upward projections 476 and 478.

Figure 40:
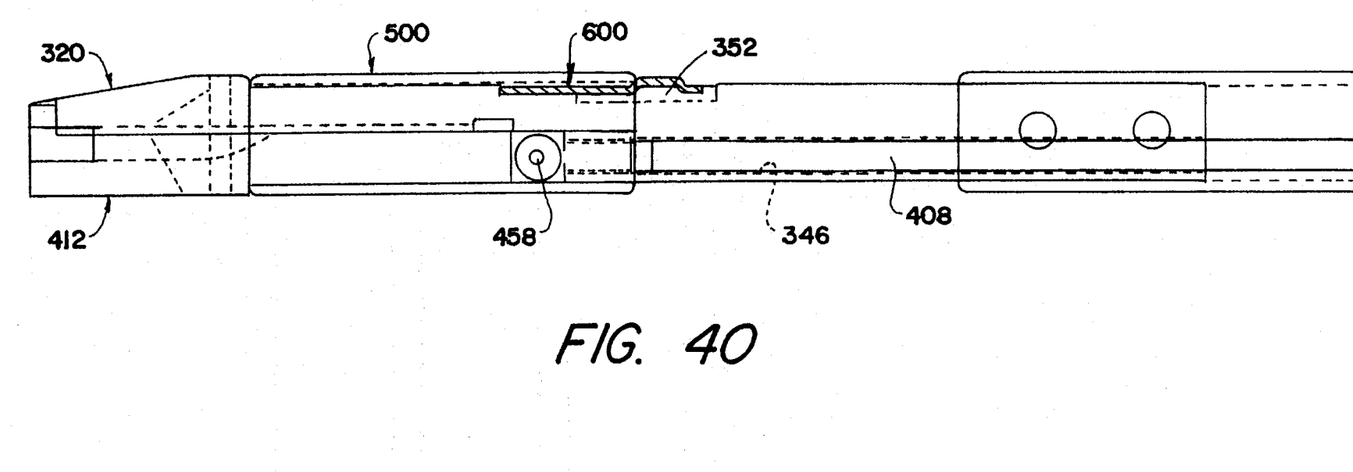
FIG. 40 is an enlarged left side elevational view of the first and second distal tips, including a locking sleeve holding the first and second tips in their mated configuration.
Figure 41:
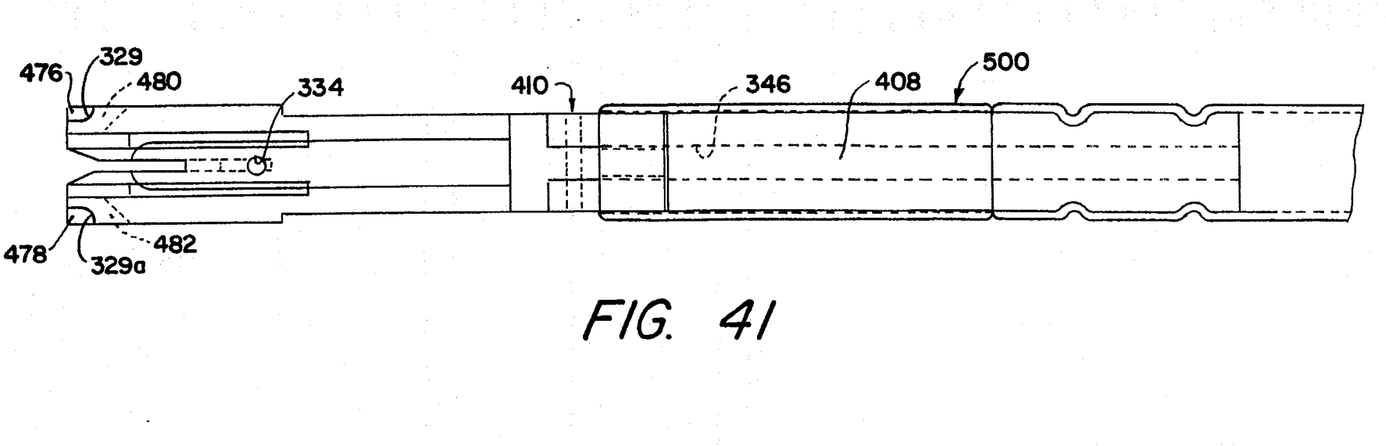
FIG. 41 is an enlarged top elevational view of the first and second distal tips shown in FIG. 40, as well as the locking sleeve, with the locking sleeve being positioned so as to allow the second tip to be pivoted away from the first tip.
Figure 42:
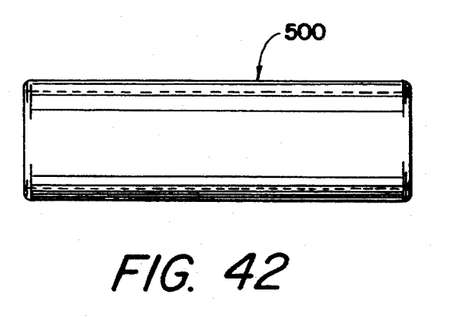
FIG. 42 is a side elevational view of the locking sleeve shown in FIGS. 40 and 41.
Figure 43:
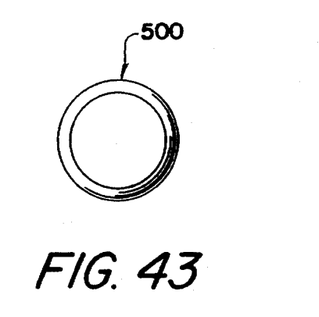
FIG. 43 is an end elevational view of the locking sleeve shown in FIG. 42.
Figure 44:
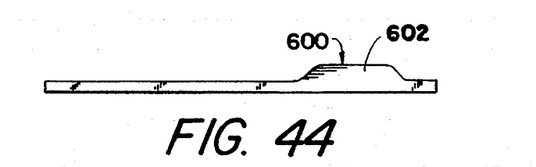
FIG. 44 is a left side elevational view of a spring adapted to be mounted to the first distal tip so as to maintain the axial location of the sleeve shown in FIGS. 42 and 43 relative to the first and second tips.
Figures 45, 47:
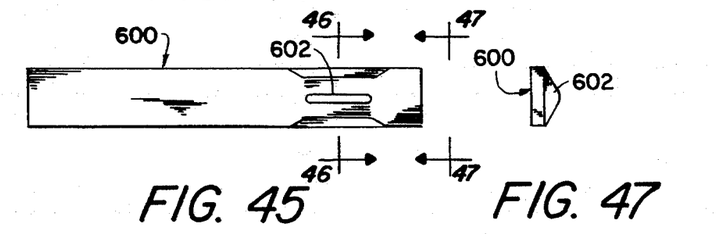
FIG. 45 is a top elevational view of the spring shown in FIG. 44.
FIG. 47 is a right end view of the spring shown in FIG. 45, taken along line 47—47 of FIG. 45.
Figure 46:
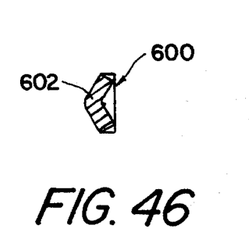
FIG. 46 is a cross-sectional view of the spring shown in FIG. 45, taken along line 46—46 of FIG. 45.

Given the foregoing detailed description of the various subassemblies which form the preferred embodiment of the suture rundown tool of the present invention, the overall tool assembly depicted in FIGS. 1–6 and the detailed views of FIGS. 40–41 will now be more easily understood. Specifically, it will be seen in FIG. 5 that the proximal portion of shaft 300 is located in the cavity defined by the internal channel portions 218 and 218a of the handle halves 202 and 204, and that the pin 104 extending through the hole 216a in the left handle half, then through the hole 310 in tubular member 302 and finally into the hole 216 in the right handle half effectively locks the positions of the shaft and the handle relative to each other.

Similarly, the connecting rod/connecting plate 406/406 assembly is located within shaft 300 and biased toward its proximalmost position by a helical spring 2 attached at one end 3 to pin 104 and at the other end 4 to hole 420 in connecting plate 406. Trigger member 402 is pivoted in the opening created by the mating depressions 220 and 220a in the handle halves 202 and 204 on pin 102 which extends through hole 214a in left handle half 204, through bore 428 in trigger 402 and into hole 214 in right handle half 202. The projection 404 from trigger 402 extends into slot 424 in connecting plate 406 such that an appropriate force applied to the trigger will pivot the trigger around pin 102, moving projection 404 against connecting plate 406 so as to drive connecting rod 408 distally relative to handle 200, thereby shifting the distal end of second distal tip 412 distally relative to the distal end of first distal tip 320.

Further, the mating engagement of the first distal tip 320 with the second distal tip 412 will now be apparent to those skilled in the art. Specifically, the downwardly extending projections 340 and 342 from first distal tip 320 slidably engage the corresponding slots 471a and 471b in second distal tip 412. The upwardly extending projections 476 and 478 from the second distal tip 412 fit within the corresponding cut away portions 329 and 329a of the distally projecting arms 331 and 333 of first distal tip 320. Further, the grooves 480 and 482 of second distal tip 412 in conjunction with the arms 331 and 333 of first distal tip 320 form closed passageways 800 (FIG. 49) in the combined tip assembly when the connecting rod 408 is in its proximalmost position. Grooves 480 and 482 form the floors of these closed passageways 800.

In the embodiment shown, a suture trimming capability also is provided. Hence, the second distal tip 412 is pivoted on hinge 410 so as to allow it to be swung away from the lower surface of first distal tip 320. A cutting blade 700 (see FIG. 50) is received in groove 356 (FIG. 22) in first distal tip 320.

The latter structure requires the provision of means for selectively (a) retaining the first and second distal tips 320, 412 in their longitudinally aligned configuration, or (b) allowing second distal tip 412 to pivot away from first distal tip 320 so as to expose the cutting blade, e.g., for replacement. This is accomplished by the provision of locking sleeve 500, best seen in FIGS. 42-43, which is disposed about the distal tip assembly. In the preferred case, a leaf spring 600, best seen in FIGS. 44-47, is located in depression 352 in the upper surface of first distal tip 320. The sleeve 500 may then be securely selectively located in one of two positions. In the first of these positions, shown in FIG. 40, the sleeve surrounds the first and second distal tips between the proximally facing shoulders 336 (FIG. 18) and 462 (FIG. 30) and the upwardly projecting portion 602 of the leaf spring 600 (FIGS. 44-47). Spring 600 may be fixedly disposed in depression 352 in any convenient manner, for example, the spring may engage undercut portions of the depression 352 or be otherwise mechanically affixed therein.

In the second position, best seen in FIG. 41, the sleeve 500 has been forced proximally over the upwardly extending portion 602 of leaf spring 600 so as to reside proximally of the hinged attachment between second distal tip 412 and connecting rod 408. In this second position, the second distal tip 412 can be swung away from first distal tip 320 so as to reveal the blade cavity. Aligned transverse bores 334 (FIG. 20) and 464 (FIG. 36) provide a means by which the surgeon can visually verify the presence of a blade between the first and second distal tips prior to the initiation of (or during) a suturing procedure.

Figure 48:
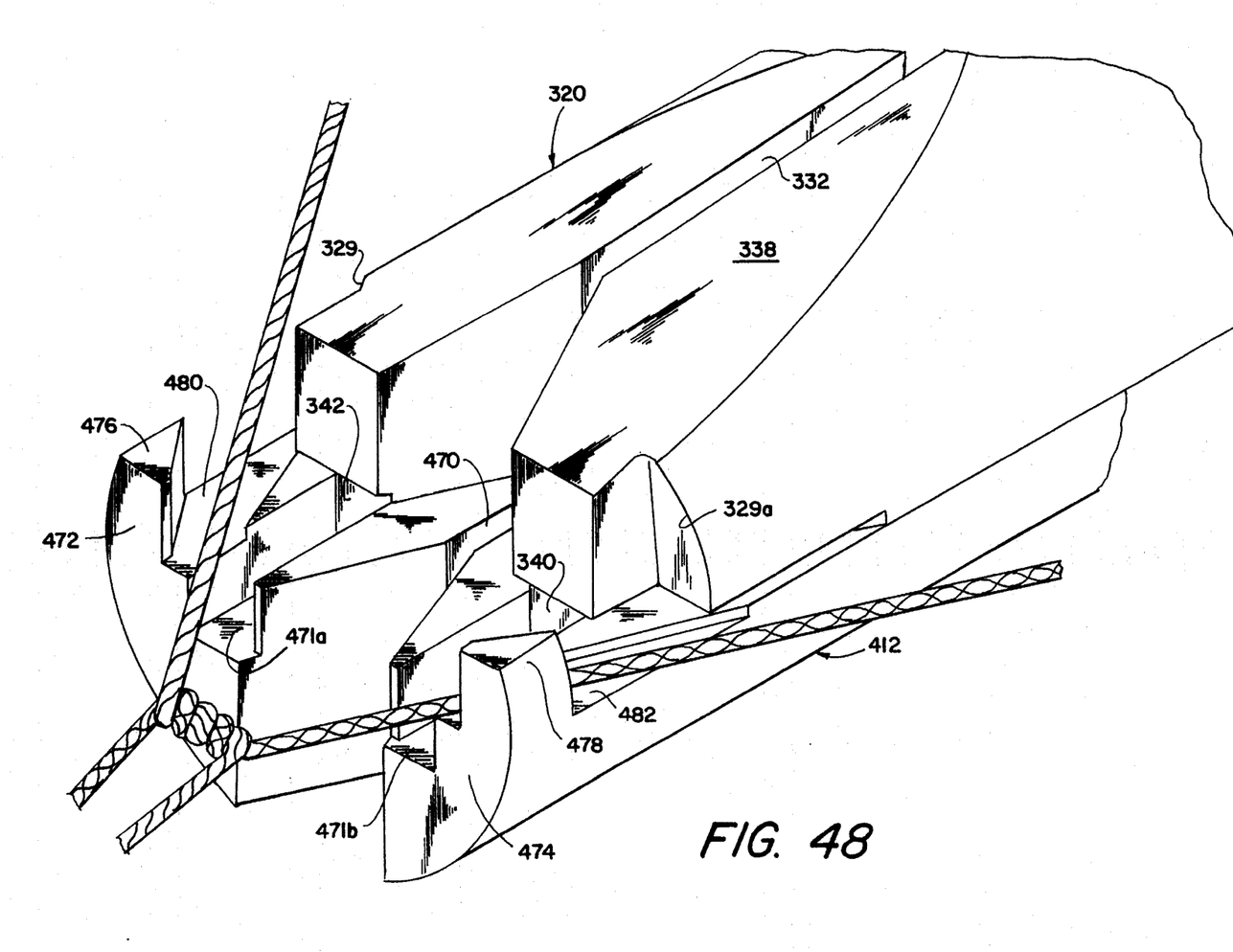
FIG. 48 is a schematic view of the distal portion of the suture rundown tool, showing the second tip shifted distally relative to the first tip, and having a suture throw positioned in front of the tool, with the suture ends extending through the grooves formed in the upper surface of the second tip.

The use of the improved suture rundown tool of the present invention will now be described with reference to FIGS. 48-50. Starting from a pair of free suture ends extending outwardly from an internal surgical site through a passageway or portal such as a cannula, the operation of the present invention includes the following steps:

(1) a suture throw is formed in the free suture ends outside of the surgical cavity;

(2) the translation means 400 are manipulated by the application of force to the proximal end of the trigger 402 so as to move the connecting rod 408 from its proximalmost position to its distalmost position, thereby shifting the second distal tip 412 distally relative to the first distal tip 320;

(3) the suture throw is positioned adjacent the distal end of the second distal tip 412 and the free suture ends are placed in the angled grooves 480 and 482 which extend between the distal end of the second distal tip 412 and the side edges thereof (see FIG. 48);

(4) the trigger 402 is released so as to allow the second distal tip 412 to be moved proximally by the biasing spring 2 to a position relative to the first distal tip wherein: (i) the downwardly extending projections 340 and 342 of first distal tip 320 located in the longitudinal grooves 471a and 471b of second distal tip 412 bear against the surgical throw, and (ii) the free suture ends extending from the opposite sides of the surgical throw extend through passageways 800 which are defined by the grooves 480 and 482 and the lower surfaces of the first distal tip 320 (see FIG. 49);

(5) the suture throw is run down the suture lengths which extend from the surgical site by pushing on the handle 200 of the tool until the suture throw reaches the desired position;

(6) then, either before or after the tool has been withdrawn from the surgical cavity, the trigger 402 is again depressed relative to the handle so as to slide second distal tip 412 distally relative to first distal tip 320, thereby permitting the suture ends to be disengaged from the tool 9 (see FIG. 48); and (7) the foregoing procedure is repeated as many times as is required to form the desired surgical knot.

Figure 49:
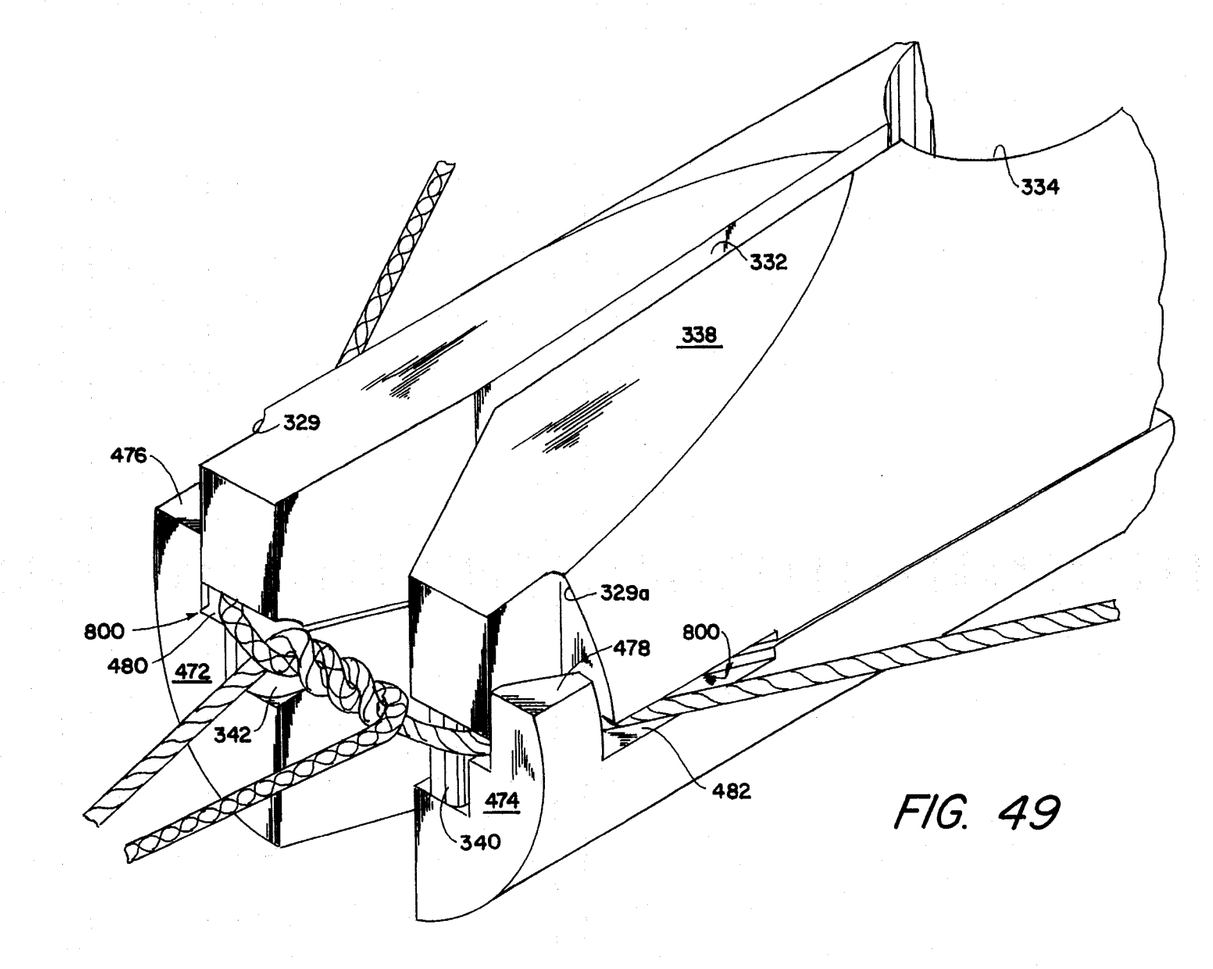
FIG. 49 is a schematic view similar to that of FIG. 48, except that the first and second tips are shown in their closed, aligned position, and having a suture throw positioned in front of the distal end of the tips, with the suture ends extending through passageways formed by the distal end of the suture rundown tool.
Figure 50:
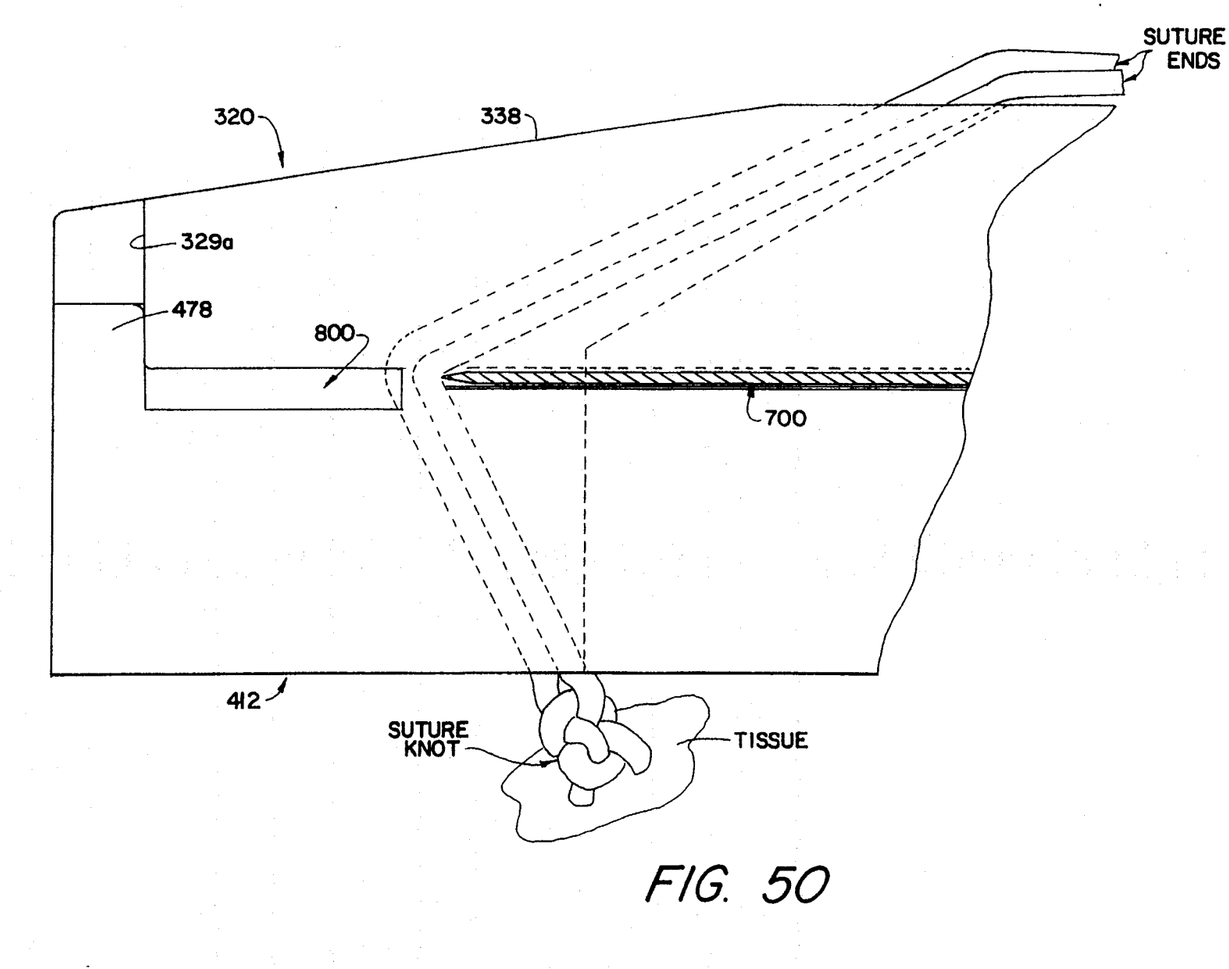
FIG. 50 is a schematic side elevational view showing a pair of free suture ends extending away from a surgical knot and through corresponding transverse slots in the first and second distal tips so as to be in cutting relation with a blade carried between the first and second tips.

Upon the release of the final suture throw from the suture throw rundown tool, (i) the trigger is released so as to allow the first and second distal tips to move into alignment with one another (see FIG. 49); (ii) the orientation of the tool (relative to the suture ends extending from the surgical knot) is rotated 90 degrees by rotating the handle about the longitudinal axis of the shaft; and (iii) the two ends of the suture extending from the knot are drawn into the slots 332 and 470 so as to bear against the cutting edge of blade 700 so as to thereby trim away the suture ends adjacent to the formed surgical knot (see, FIG. 50).

It should be understood that the foregoing specification is intended to be illustrative only, and not limiting of the invention in its broadest aspects. Numerous variations, adaptations, changes and modifications of the improved suture rundown tool of the present invention will occur to those skilled in the art and are considered to be within the scope of the present invention. It is intended that the invention should be limited only by the terms of the claims appended hereto.

What is claim is:

1. A method of running a suture throw down free ends of suture extending from an operative site into engagement with the operative site, comprising the steps of:

(a) providing a suture throw rundown tool comprising:

a handle;

an elongated shaft having a longitudinal axis, a proximal end and a first distal tip having a first distal end, said shaft defining a hole therein substantially adjacent said proximal end, and said proximal end being located within and fixedly attached to said handle;

a rod having a proximal end and a second distal tip having a second distal end, said rod extending through said shaft in reciprocable longitudinal relation therewith;

helical spring means having a first end and a second end located within said shaft substantially adjacent its proximal end;

pin means extending through said handle and said hole in said shaft so as to secure said shaft to said handle, said first end of said spring being attached to said pin and said second end of said spring being attached to said proximal end of said rod; and actuation means for moving said rod relative to said shaft between a proximalmost position and a distalmost position;

said first and second distal tips being so configured as to mate with each other in longitudinally reciprocal relation such that:

(i) when said rod is in said proximalmost position, said first distal end of said first distal tip and said second distal end of said second distal tip are aligned with one another, and said first and second distal tips together define a distally facing suture throw engagement portion flanked by a pair of passageways, each of said passageways (a) being sized to receive a length of suture in sliding relation therethrough, (b) extending respectively from said suture engagement portion at an acute angle to said longitudinal axis through said mated, aligned first and second distal tips, and (c) being formed by the alignment of a first portion located in said first distal tip and a second portion located in said second distal tip; and (ii) when said rod is in said distalmost position, said second distal end of said second distal tip is offset distally relative to said first distal end of said first distal tip by a distance at least equal to the length of said passageways measured along said longitudinal axis;

(b) forming a suture throw in the free ends of suture extending from an operative site;

(c) manipulating said actuation means so as to place said rod in its distalmost position;

(d) engaging said throw with said second distal end of said second distal tip and placing said free suture ends extending from said throw respectively into passageway portions flanking said second distal end of said second distal tip;

(e) manipulating said actuation means so as to move said rod from said distalmost position to said proximalmost position, thereby slidably capturing said free suture ends extending from said throw respectively in said flanking passageways and engaging said throw with said throw engagement portion formed by said first and said second distal tips;

(f) running said throw down said suture ends extending from said operative site to said operative site;

(g) manipulating said actuation means so as to move said rod to its distalmost position and releasing said free ends of suture extending from said throw from said second passage forming portions; and (h) repeating steps (b) through (g) as many times as necessary to complete the formation of the desired surgical knot at the internal surgical site.

2. A method according to claim 1 wherein said shaft further defines an opening located distally of said hole, said handle defines an open slot and said actuation means comprises a trigger assembly pivotally mounted to said handle in said slot on a second pin, said trigger assembly comprising a trigger and a projection extending from said trigger so as to engage said rod such that a force directed inwardly against said trigger will rotate said trigger about said second pin and cause said projection to urge said rod toward its distalmost position.

3. A method according to claim 1 wherein:

said first distal tip defines first and second recessed portions on opposite sides of said first distal end, and a first substantially planar mating surface having a pair of spaced first projections extending normally outwardly therefrom adjacent said first distal end; and said second distal tip defines a second substantially planar mating surface having:

(i) a pair of spaced longitudinal slots therein extending proximally from said second distal end;

(ii) a pair of second projections extending normally outwardly therefrom, said projections being located on opposite sides of said surface immediately adjacent said second distal end; and (iii) a pair of grooves, each said groove extending from said second distal end to an adjacent side edge of said second mating surface substantially immediately proximally of one of said second projections.

4. A method according to claim 1 wherein said first distal end and said second distal end define corresponding slots extending proximally from said first and second distal ends respectively to proximal slot ends, said slots each being located normal to both the distal end and the substantially planar mating surface of its associated distal tip, and a cutting blade having a cutting edge is fixedly disposed between said first and second distal tips such that said cutting edge extends distally of said proximal ends of said slots, and including the step after step (h) of drawing said free suture ends extending from said knot into said corresponding slots and severing same with said cutting edge.

5. A method according to claim 4 wherein said second distal tip is hingedly attached to said rod and a sleeve member closely surrounds said tool, said sleeve being movable between a first position closely surrounding said first and second distal tips and a second position located proximally of said hinged attachment of said second distal tip to said rod.

6. A method according to claim 5 wherein said suture rundown tool further comprises means for releasably locking said sleeve in said first or said second position.

7. A method according to claim 6 wherein said locking means comprises a distally facing shoulder extending around said shaft, a proximally facing shoulder extending around said mated first and second distal tips when said first and second distal ends of said first and second distal tips are aligned with each other, said proximally facing shoulder and said distally facing shoulder being longitudinally separated from each other by a longitudinal distance slightly greater than twice the axial length of said sleeve, and flexible projecting means extending radially outwardly from said first distal tip proximally of said hinged attachment of said second distal tip to said rod when said first distal end of said first distal tip is aligned with said second distal end of said second distal tip such that said sleeve may be forced from a first position engaging said proximally facing shoulder over said flexible projection to a second position engaging said distally facing shoulder and vice versa.

8. A suture throw rundown tool comprising:
a handle;
an elongated shaft having a longitudinal axis, a proximal end and a first distal tip having a first distal end, said shaft defining a hole therein substantially adjacent said proximal end, and said proximal end being located within and fixedly attached to said handle;
a rod having a proximal end and a second distal tip having a second distal end, said rod extending through said shaft in reciprocable longitudinal relation therewith;
helical spring means having a first end and a second end located within said shaft substantially adjacent its proximal end;
pin means extending through said handle and said hole in said shaft so as to secure said shaft to said handle, said first end of said spring being attached to said pin and said second end of said spring being attached to said proximal end of said rod; and
actuation means for moving said rod relative to said shaft between a proximalmost position and a distalmost position;
said first and second distal tips being so configured as to mate with each other in longitudinally reciprocal relation such that:
 (i) when said rod is in said proximalmost position, said first distal end of said first distal tip and said second distal end of said second distal tip are aligned with one another, and said first and second distal tips together define a distally facing suture throw engagement portion flanked by a pair of passageways, each of said passageways (a) being sized to receive a length of suture in sliding relation therethrough, (b) extending respectively from said suture engagement portion at an acute angle to said longitudinal axis through said mated, aligned first and second distal tips, and (c) being formed by the alignment of a first portion located in said first distal tip and a second portion located in said second distal tip; and
 (ii) when said rod is in said distalmost position, said second distal end of said second distal tip is offset distally relative to said first distal end of said first distal tip by a distance at least equal to the length of said passageways measured along said longitudinal axis.

9. A suture rundown tool according to claim 8 wherein said shaft further defines an opening located distally of said hole, said handle defines an open slot and said actuation means comprises a trigger assembly pivotally mounted to said handle in said slot on a second pin, said trigger assembly comprising a trigger and a projection extending from said trigger so as to engage said rod such that a force directed inwardly against said trigger will rotate said trigger about said second pin and cause said projection to urge said rod toward its distalmost position.

10. A suture rundown tool according to claim 8 wherein:
said first distal tip defines first and second recessed portions on opposite sides of said first distal end, and a first substantially planar mating surface having a pair of spaced first projections extending normally outwardly therefrom adjacent said first distal end; and
said second distal tip defines a second substantially planar mating surface having:
 (i) a pair of spaced longitudinal slots therein extending proximally from said second distal end;
 (ii) a pair of second projections extending normally outwardly therefrom, said projections being located on opposite sides of said surface immediately adjacent said second distal end; and
 (iii) a pair of grooves, each said groove extending from said second distal end to an adjacent side edge of said second mating surface substantially immediately proximally of one of said second projections.

11. A suture rundown tool according to claim 8 wherein said first distal end and said second distal end define corresponding slots extending proximally from said first and second distal ends respectively to proximal slot ends, said slots each being located normal to both the distal end and the substantially planar mating surface of its associated distal tip, and a cutting blade having a cutting edge is fixedly disposed between said first and second distal tips such that said cutting edge extends distally of said proximal ends of said slots.

12. A suture rundown tool according to claim 11 wherein said second distal tip is hingedly attached to said rod and a sleeve member closely surrounds said tool, said sleeve being movable between a first position closely surrounding said first and second distal tips and a second position located proximally of said hinged attachment of said second distal tip to said rod.

13. A suture rundown tool according to claim 12 further comprising means for releasably locking said sleeve in said first or said second position.

14. A suture rundown tool according to claim 13 wherein said locking means comprises a distally facing shoulder extending around said shaft, a proximally facing shoulder extending around said mated first and second distal tips when said first and second distal ends of said first and second distal tips are aligned with each other, said proximally facing shoulder and said distally facing shoulder being longitudinally separated from each other by a longitudinal distance slightly greater than twice the axial length of said sleeve, and flexible projecting means extending radially outwardly from said first distal tip proximally of said hinged attachment of said second distal tip to said rod when said first distal end of said first distal tip is aligned with said second distal end of said second distal tip such that said sleeve may be forced from a first position engaging said proximally facing shoulder over said flexible projection to a second position engaging said distally facing shoulder and vice versa.

* * * * *